US00RE44367E

(19) United States
(12) Reissued Patent
Aonuma

(10) Patent Number: US RE44,367 E
(45) Date of Reissued Patent: Jul. 16, 2013

(54) IMAGE AND INFORMATION PROCESSOR

(75) Inventor: Masashi Aonuma, Kanagawa (JP)

(73) Assignee: FUJIFILM Corporation, Tokyo (JP)

(21) Appl. No.: 13/548,564

(22) Filed: Jul. 13, 2012

Related U.S. Patent Documents

Reissue of:
(64) Patent No.: 6,762,429
Issued: Jul. 13, 2004
Appl. No.: 09/989,407
Filed: Nov. 21, 2001

(30) Foreign Application Priority Data

Nov. 21, 2000 (JP) ..... 2000-354014

(51) Int. Cl.
*G03B 42/02* (2006.01)

(52) U.S. Cl.
USPC ..... 250/583; 250/582; 715/201

(58) Field of Classification Search
USPC ..... 250/582, 583; 715/201
See application file for complete search history.

(56) References Cited

U.S. PATENT DOCUMENTS

| | | | | |
|---|---|---|---|---|
| 4,739,480 | A | 4/1988 | Oono et al. | |
| 4,789,782 | A | 12/1988 | Ohara | |
| 5,646,416 | A | 7/1997 | Van de Velde | |
| 5,654,555 | A | 8/1997 | Buytaert et al. | |
| 5,757,021 | A | 5/1998 | Dewaele | |
| 6,335,796 | B1 | 1/2002 | Endo et al. | |
| 6,359,628 | B1 | 3/2002 | Buytaert | |
| 6,504,897 | B1 * | 1/2003 | Yonekawa | 378/63 |
| 6,528,810 | B1 | 3/2003 | Toda | |
| 6,993,114 | B2 | 1/2006 | Takasawa | |
| 7,239,405 | B2 | 7/2007 | Yamade et al. | |
| 2002/0131625 | A1 | 9/2002 | Vining et al. | |
| 2003/0107777 | A1 * | 6/2003 | Yamade et al. | 358/442 |

FOREIGN PATENT DOCUMENTS

| | | | |
|---|---|---|---|
| JP | 63-253348 | A | 10/1988 |
| JP | 01-227139 | A | 9/1989 |
| JP | 04-123173 | A | 4/1992 |

(Continued)

OTHER PUBLICATIONS

Notification of Reasons for Refusal, issued Jan. 27, 2009, issued in corresponding JP Application No. 2000-354014, 4 pages in English and Japanese.

(Continued)

*Primary Examiner* — Constantine Hannaher
(74) *Attorney, Agent, or Firm* — Sughrue Mion, PLLC

(57) ABSTRACT

The image and information processor includes an image information processing unit having a function for inputting patient information and radiation image capture information related to the patient information, a function for receiving a first radiation image having been read by a radiation image reading device and a function for performing image processing on the first radiation image, an image display device for the displaying at least one of the first radiation image and second radiation image having been subjected to the image processing and an external storage device for temporarily storing at least one of the first radiation image and the second radiation image in relation to the patient information; wherein the image information processing unit is constructed such that a serial radiography based on a plurality of radiographic conditions of the image capture information relating to one patient inputted by the input function can be reserved as a single inspection. The image information processing unit may be connected via a network to one or more radiation image reading devices and one or more image output devices for outputting the second radiation images.

15 Claims, 8 Drawing Sheets

FOREIGN PATENT DOCUMENTS

| | | | |
|---|---|---|---|
| JP | 04-155581 | A | 5/1992 |
| JP | 06-186654 | A | 7/1994 |
| JP | 10-232922 | A | 9/1998 |
| JP | 10-260486 | A | 9/1998 |
| JP | 11-252326 | A | 9/1999 |
| JP | 2000-092439 | A | 3/2000 |
| JP | 2000-099688 | A | 4/2000 |
| JP | 2000-166908 | A | 6/2000 |

OTHER PUBLICATIONS

Notification of Reasons for Refusal, issued May 26, 2009, issued in corresponding JP Application No. 2000-354014, 4 pages in English and Japanese.

* cited by examiner

FIG.4 AMENDED
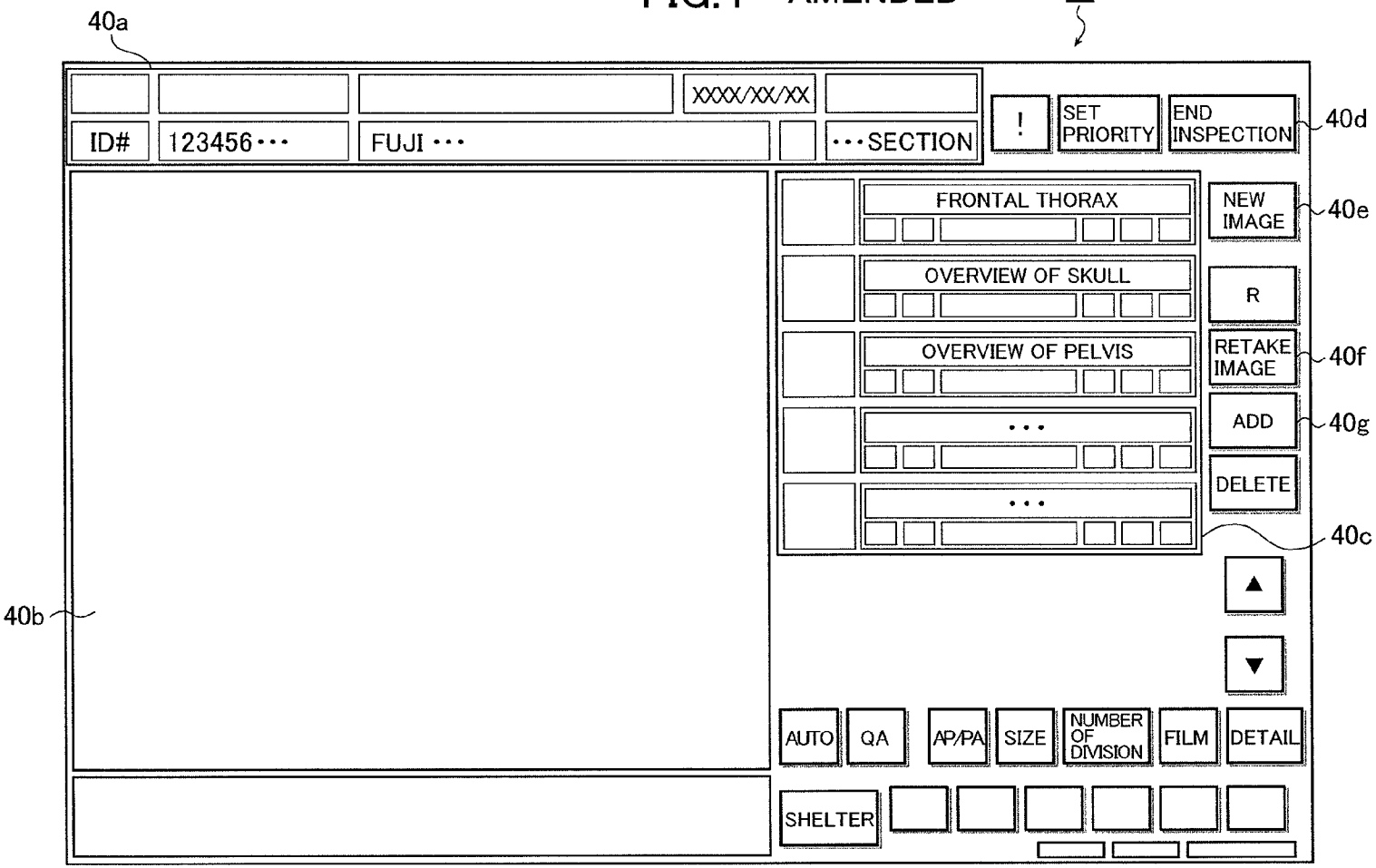

IMAGE AND INFORMATION PROCESSOR

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to an image and information processor, and more specifically to an image and information processor for images and information for medical treatment purposes, which is a standalone (i.e., independent) device or which is used by being connected to a network.

2. Description of the Related Art

Currently, a radiation image information recording and reproducing system is being used which utilizes a stimulable phosphor, and according to this system, when an irradiation of radiation (i.e., X-rays, α-rays, β-rays, γ-rays, electronic beams, ultra-violet rays or the like) is received, a portion of the radiation energy of this irradiation is stored, and then when an irradiation of laser light or visible light or other such excitation light is received, the stimulable phosphor shows a photostimulated luminescence as a result of the stored energy.

Examples of this type of radiation image information recording and reproducing system include, for example, systems such as those proposed in JP 63-253348 A, JP 01-227139 A, JP 04-123173 A and JP 04-155581 A by the present Assignee. In such a system, an image of a patient is captured at a hospital, for example, by means of an X-ray image capturing device or the like, radiation image information pertaining to this patient, for example, is stored and recorded on a sheet of a stimulable phosphor, and this sheet is scanned by means of a laser or other such excitation light to generate photostimulated luminescence light; and the system is provided with a radiation image reading device for photoelectronically reading the photostimulated luminescence light which has been obtained in this way and thereby obtaining image data; an identification information registration device for registering the patient's identification information; and an image recording device for recording a radiation image onto a photographic photo-sensitive material or other such recording material, for example, as a visible image based on the obtained image data, in connection with the registered patient's identification information and the like.

In this type of conventional radiation image information processing system, before the image of the patient is captured or at the time when the image is captured, identification (i.e., ID) information is registered in the identification information registration device (i.e., ID terminal) which is positioned proximate to the radiation image capturing device and the like; this identification information being comprised of the patient's first and last name, sex, date of birth, identification (i.e., ID) number and other such information pertaining to the patient, along with the year, month and date on which the image was captured, the region that was captured, the method by which the image was captured, a bar code information from the stimulable phosphor sheet onto which the image was captured, and other such information relating to the capturing of the image.

On the other hand, information such as the following is sent from the ID terminal to the radiation image reading device: the registered identification information and conditions for the processing of the radiation image which has been read by the radiation image reading device; an output destination for the processed radiation image (i.e., a destination to which the image data is to be distributed), meaning information regarding which image recording device the image data should be outputted to; the output conditions for outputting the processed radiation image from the image recording device; and also a distribution destination for the outputted radiation image, such as an internist's office or surgeon's office or other such particular medical specialist's office in a hospital, for example.

Also, the radiation image reading device reads the bar code on the back surface of the stimulable phosphor sheet and establishes a correspondence (relationship) with the patient's ID information which has been obtained from the ID terminal, and also reads from the stimulable phosphor sheet the radiation image information which was captured onto this stimulable phosphor sheet, performs the image processing and the like in accordance with the conditions which have been received and sends to the image recording device the processed radiation image which has thus been produced, outputting this image together with the output conditions. At the image recording device, the processed radiation image is outputted, according to the obtained output conditions, as a transparent film image equivalent to an X-ray image or reflective paper image or other such hard copy image. The outputted radiation image is distributed by means of a well known means to the distribution destination which was obtained from the ID terminal.

In the conventional radiation image information processing system disclosed in the above-mentioned publications, the radiation image reading device can read vast amounts of the stimulable phosphor sheet, and due to reduced costs, it is possible to use a plurality of radiation image reading devices; accordingly, not only is it possible to connect one of or a plurality of the radiation image reading devices to a plurality of ID terminals and position the ID terminals close to the radiation image capturing device, but also it is possible to place the ID terminals close to the reception desk or other part of the hospital or the various specialists' offices, for example, thereby improving the ease and efficiency of the inputting of the patient information and the cross-checking of the patient information against the stimulable phosphor sheet at the capturing device. Alternatively, it becomes possible to perform the reading of the stimulable phosphor sheet by any radiation image reading device, regardless of which ID terminal the stimulable phosphor sheet was registered in, thus enabling the efficient running of a plurality of radiation image reading devices Further, in the conventional radiation image information processing system disclosed in the above-mentioned publications, it is possible to connect a plurality of ID terminals, which are connected to one or more radiation image reading devices, or a plurality of ID terminals which are each individually connected to one of a plurality of radiation image reading devices to a single managing device (such as a host computer or manager ID terminal), or connect a plurality of radiation image reading devices to a single ID information input storage unit, and thus realize integrated management of the ID information, and also it becomes possible to perform integrated management of the running status of the radiation image reading device and the image recording device, and the usage status of the stimulable phosphor sheet, and thus manage the efficient running of the radiation image reading device and the efficient use and longevity of the stimulable phosphor sheet and the like. At this time, one or more image recording device may be connected to the one or more radiation image reading devices, and thus the efficient running of the image recording device is enabled.

However, in recent years, even in this type of conventional radiation image information processing system, what is used for the image output device, which outputs the radiation image as a visible image, is not only an image recording device for recording onto the recording material, but also an image display device for performing a monitor-type display on an LCD, CRT or the like for review of the radiation image. Also, this type of image display device is now physically set up as in image review device in each specialists' office in the hospital or such, and is also set up for each physician, image inspection engineer or other type person who is to inspect the image.

Therefore, not only is the outputted hard copy image distributed to the particular specialist's office in the hospital or other such distribution destination, but also, in order to make the diagnosis more efficient, to shorten the amount of time that the patient has to wait and to speed up the medical care, the radiation image which has been read by the radiation image reading device and has been subjected to the image processing and the like is now also sent as image data for review (i.e., display) purposes to such distribution destinations as the image review devices and the like which are set up at each specialist's office or set up for each person who is to inspect the image.

In the conventional radiation image information processing system described above, the image is handled ultimately in per-image units, and it must be recognized that in recent years this has become an inconvenience since a single inspection has now come to involve several images or more.

SUMMARY OF THE INVENTION

The present invention is to be developed in light of this development whereby several images or more are used in a single inspection, and an object of the present invention is to provide an image and information processor in which the images are not handled in per-image units, but are handled in units of the several or more images to be used in the single inspection.

In order to attain the object described above, the present invention provides an image and information processor comprising: an image information processing unit having a function for inputting patient information and radiation image capture information related to the patient information; a function for receiving at least one first radiation image having been read by means of a radiation image reading device; and a function for performing image processing on the at least one first radiation image having been received from the radiation image reading device; an image display device which is connected to the image information processing unit and displays at least one of the at least one first radiation image and at least one second radiation image having been subjected to the image processing by the image information processing unit; and an external storage device which is connected to the image information processing unit and stores temporarily at least one of the at least one first radiation image and the at least one second radiation image in relation to the patient information; wherein the image information processing unit is constructed such that a serial radiography based on a plurality of radiographic conditions of the image capture information relating to one patient inputted by means of the input function can be reserved as a single inspection, *the plurality of radiographic conditions of the radiation image capture information which are reserved as the single inspection are displayed in a single screen of the image display device as tags, each corresponding to each of the plurality of radiographic conditions, each of predetermined regions corresponds in a one-to-one manner to each of the tags and displaying a thumbnail image of a radiation image corresponding to each of the plurality of radiographic conditions, is displayed in advance adjacent to a region in which each of the plurality of radiographic conditions is displayed, and, when the serial radiography is begun and the radiation image corresponding to each of the plurality of radiographic conditions is stored, a thumbnail image of the radiation image is displayed in a predetermined region of the predetermined regions corresponding to a tag of the tags.*

Preferably, the image information processing unit is connected via a network to the radiation image reading device or radiation image reading devices and one or more image output devices for outputting the at least one second radiation image.

[Preferably, the plurality of radiographic conditions of the radiation image capture information which are reserved as the single inspection are displayed in a single screen as tags, each corresponding to each of the plurality of radiographic conditions.]

[Preferably, when the serial radiography is begun and the radiation image corresponding to each of the plurality of radiographic conditions is stored, a thumbnail image of the radiation image is displayed in relation to a tag of the tags.]

Preferably, a relationship between the tag and the thumbnail image can be altered or exchanged by moving the thumbnail image that has been displayed related to the tag.

Preferably, consecutive numbers are assigned to radiation images pertaining to the single inspection according to order that the tags are arranged in, and this display sequence in which the radiation images are displayed is controlled by the consecutive numbers.

Preferably, consecutive numbers are assigned to radiation images pertaining to the single inspection according to order that the tags are arranged in, and when the radiation images are outputted, this output sequence is controlled by the consecutive numbers.

*Preferably, the single inspection is reserved based on an inspection prescription.*

*Preferably, the plurality of radiographic conditions of the image capture information include at least one of a region of a patient to be captured, a direction from which the at least one first radiation image is to be captured, an orientation for image capture, and size.*

*Preferably, an order of image capture conditions progresses in order of difficulty of image capture.*

In order to attain the object described above, the present invention provides an image and information processor, comprising; the one or more radiation image reading devices for reading a radiation image; an image information processing unit having a function for inputting patient information and radiation image capture information related to the patient information; a function for receiving at least one first radiation image having been read by means of one or more radiation image reading devices; and a function for performing image processing on the at least one first radiation image having been received from the one or more radiation image reading devices; an image display device which is connected to the image information processing unit and displays at least one of the at least one first radiation image, and at least one second radiation image having been subjected to the image processing by the image information processing unit; and an external storage device which is connected to the image information processing unit and stores temporarily at least one of the at least one first radiation image and the at least one second radiation image in relation to the patient information; wherein the image information processing unit is connected via a network to the one or more radiation image reading devices and one or more image output devices for outputting the at least one second radiation image; and wherein the image information processing unit is constructed such that a serial radiography based on a plurality of radiographic conditions of the radiation image capture information relating to one patient inputted by means of the input function can be reserved as a single inspection, *the plurality of radiographic conditions of the radiation image capture information which are reserved as the single inspection are displayed in a single screen as tags, each corresponding to each of the plurality of radiographic conditions, each of predetermined regions corresponds in a one-to-one manner to each of the tags and displaying a thumbnail image of a radiation image corresponding to each of the plurality of radiographic conditions, is displayed in advance in a region adjacent to a region in which each of the plurality of radiographic conditions is displayed, and wherein when the serial radiography is begun and the radiation image corresponding to each of the plurality of radiographic conditions is stored, a thumbnail image of the radiation image is displayed in a predetermined region of the predetermined regions corresponding to a tag of the tags.*

*Preferably, a frame for specifying a region for displaying the thumbnail image is provided in each of the predetermined regions.*

*Preferably, nothing is displayed in each of the predetermined regions until when the radiation image corresponding to each of the plurality of radiographic conditions is stored.*

*Preferably, the predetermined regions are blank regions.*

*Preferably, a frame for specifying a region for displaying the thumbnail image is provided in each of the predetermined regions.*

*Preferably, nothing is displayed in each of the predetermined regions until when the radiation image corresponding to each of the plurality of radiographic conditions is stored.*

*Preferably, the predetermined regions are blank regions.*

BRIEF DESCRIPTION OF THE DRAWINGS

In the accompanying drawings:

FIG. 4 is a diagram depicting a specific example of an image capture screen which is outputted and displayed on a screen of an image display device inside the IIP;

DETAILED DESCRIPTION OF THE PREFERRED EMBODIMENTS

Hereinafter, explanation will be made of an embodiment of the present invention, making reference to the attached drawings.

Figure 1:
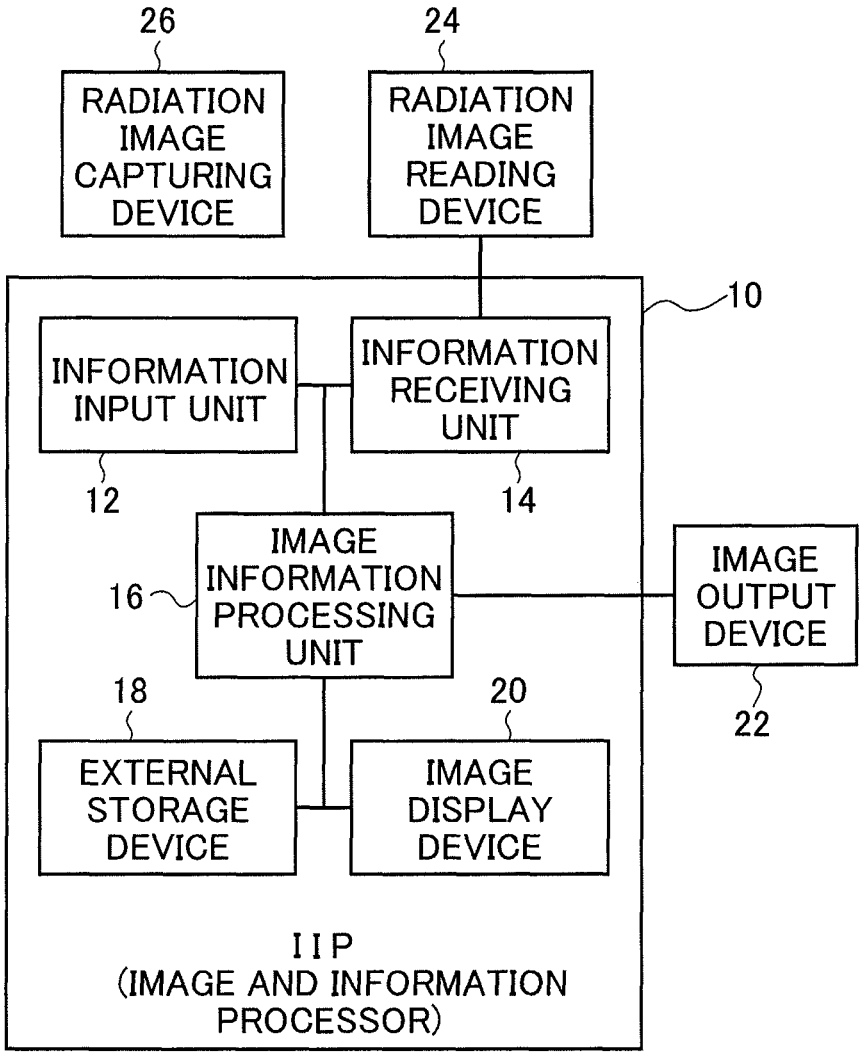
FIG. 1 is a diagram depicting an outline construction of an independent-type (stand-alone) IIP incorporating an image information processing device thereinto, according to one embodiment of the present invention.
Figure 2:
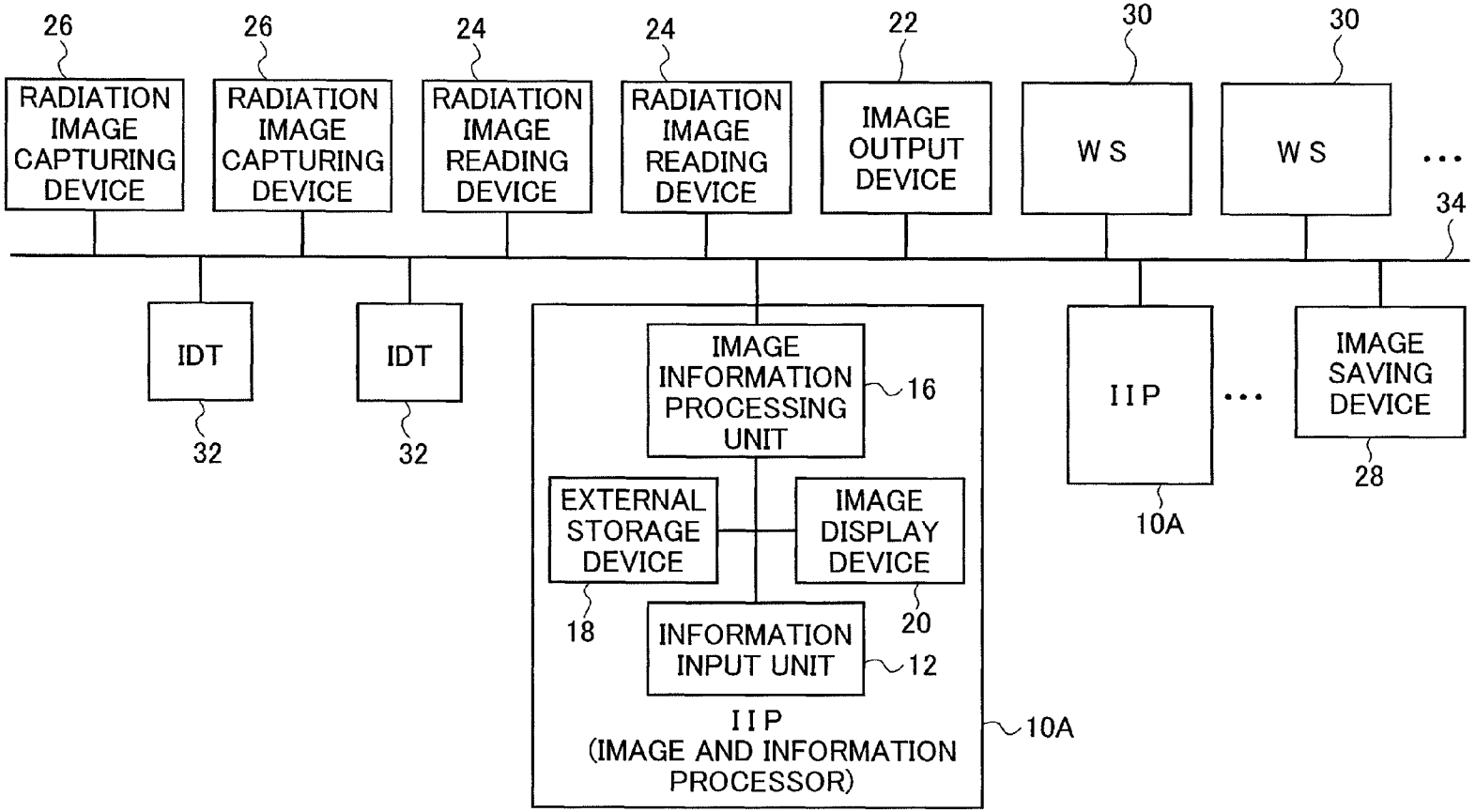
FIG. 2 is a diagram depicting an outline construction of an IIP connected to a network and incorporating the image information processing device thereinto, according to one embodiment of the present invention.

FIG. 1 is a diagram depicting an outline construction of an independent-type (i.e., stand-alone) image information processing system using an image and information processor (referred to hereinafter as IIP) according to an embodiment of the present invention, and FIG. 2 is a diagram depicting an outline construction of an image information processing system constructed by connecting via a network to the IIP according to the embodiment of the present invention.

As depicted in FIG. 1, an IIP 10 according to the first embodiment is comprised of an information input unit 12 for inputting patient information, radiation image capturing information which is related or linked to this patient information, and the like; an information receiving unit 14 for receiving the radiation image taken by means of a radiation image reading device 24 described below; an image information processing unit 16 for performing image processing on a radiation image received from the radiation image reading device 24; an external storage device 18, which is connected to the image information processing unit 16 and which temporarily stores the radiation image before or after it has been subjected to the image processing by the image information processing unit 16 in relation to the patient information; an image display device 20, which is connected to the image information processing unit 16, and which is for displaying the radiation image before and after it is subjected to the image processing. Note that reference numeral 22 indicates an image output device being connected to the above-mentioned image information processing unit 16, reference numeral 24 indicates the radiation image reading device and reference numeral 26 indicates a radiation image capturing device.

Further, as depicted in FIG. 2, an IIP 10A according to the second embodiment 2 has almost the same construction as the IIP 10 depicted in FIG. 1, and generally there are more than one of each of the following connected to the network: the IIP 10A, the image output device 22, the radiation image reading device 24, the radiation image capturing device 26, image saving device 28, a workstation (hereinafter, referred to as WS) 30 for viewing the images and the like, and an ID input terminal (hereinafter, referred to as IDT) 32.

Note that the IIP 10 and the IIP 10A depicted in FIG. 1 and FIG. 2 have mutually different formats for receiving the image from the radiation image reading device 24, but their substantial operations are exactly the same, so the explanation of the operations of the present embodiment will be made in detail regarding the image information processing system, including the IIP 10A depicted in FIG. 2.

The information input unit 12 has substantially the same functions as the IDT 32 mentioned above, and it is for inputting the patient information and the radiation image capturing information which is to be used for the inspection, and which has been linked to the patient information. Note that the patient information to be inputted (i.e., ID information) includes, for example, the patient's first and last name, sex, date of birth, ID number and the like, and the radiation image capturing information includes a year, date and month on which the image was captured, a region that was captured, a method used to capture the image, bar code information from a stimulable phosphor sheet onto which the image was captured, a distribution destination to which the radiation image is to be sent (such as the office of the specialist who requested the image), conditions for performing the image processing, and the like.

The image information processing unit 16 has such functions as a function for receiving the radiation image before it is subjected to the image processing which was read by means of the radiation image reading device 24 discussed below; a function for performing image processing on the unprocessed radiation image which has been received from the radiation image reading device 24 and not yet subjected to the image processing, this image processing being image processing which is appropriate for outputting the image, or image processing which is performed according to image processing conditions which are configured in advance in the image capturing information; and a function for distributing a radiation image which has been subjected to the image processing to at least one of the plurality of WSs 30 and the image saving device 28.

Additionally, the image processing unit 16 has a function inside this IIP 10A for storing at least the inputted patient information into the external storage device 18 in a searchable state, and then the next time and thereafter, using a part of the patient information as a search term to search the external storage device 18 to read out the corresponding patient information from the patient information stored in the external storage device 18. In the case where there was a change in the patient information it is sufficient to update this information and store it in the external storage device 18. By doing this the procedure of inputting the patient information becomes more efficient and the burden on the operator is alleviated.

The external storage device 18 is a device for linking either one of or both of the unprocessed radiation image received from the radiation image reading device 24 and the processed radiation image which has been subjected to the image processing by the image information processing unit 16 to the patient ID information including the patient information and the image capturing information which were inputted into the image information processing unit 16, and then temporarily storing these into a temporary storage device. Note that it is better to have many radiation images be temporarily stored in the external storage device 18, and further, it is better for the storage period to be long; however, these conditions are not particularly limitations, and so they may be chosen appropriately in accordance with storage capacity and costs and the scale of the hospital or such which is to use the images. Note that at least the patient information is stored in the external storage device 18, being stored in a format such that it is searchable by the image information processing unit 16, using a part of the patient information as a search term.

The image display device 20 is for displaying the patient information, the image capturing information and other such ID information which the operator has inputted and registered in advance into the image information processing unit 16, at the time when they are inputted or after they were inputted for purposes of confirmation, and further, displaying one of or both of the unprocessed radiation image received from the radiation image reading device 24 and the processed radiation image which has been subjected to image processing by the image information processing unit 16 in relation to the above-mentioned ID information, or together with a part of or all of the ID information. The image display device 20 which is to be used in the present embodiment is not particularly limited, and so a CRT display devices LCD (monitor), plasma display or other such well known display or monitor may be used; but in the case where the display device is to be used for the display of images for medical diagnosis purposes it is preferable to use an image display device which is capable of displaying high-resolution images.

The image output device 22 is for recording/outputting the processed radiation image as a visible image onto a photographic photo-sensitive material (i.e., photo-sensitive film) or the like, for example, in relation to the patient's ID information and the like, that is, by establishing a relation or a correspondence between this radiation image which is printed out as a visible image and the patient's ID information and the like. One or more of these image output devices 22 are typically connected via the network 34. Note that the image output device 22 may receive from the image information processing unit 16 and through the network 34 an image data signal for the unprocessed radiation image which was read by the radiation image reading device 24, and output this unprocessed radiation image.

The image output device to be used in the present invention is not particularly limited, but it is desirable to use a device which can perform recording and outputting of a hard copy image which has qualities which are equivalent to those of X-ray film images which are used for medical diagnosis. Typical examples of this sort of recording device include devices which scan and expose photographic photosensitive material (i.e., photosensitive film) by means of a modulated light beam such as a laser beam modified in accordance with the image data signals of the radiation image received from the image information processing unit 16, then record a latent image, expose photo-sensitive material which has been exposed by exposure processing, and then output the radiation image as a hard copy image; or devices in which the image is recorded and outputted onto heat-sensitive material (i.e., thermal film) by means of a thermal recording head ([ire.,]*i.e.,* thermal head) which is modulated in accordance with the image data signals of the radiation image, or by means of a heat mode laser which is modulated in a similar fashion.

Note the above-mentioned photo-sensitive material and heat-sensitive material is not particularly limited, either, but it is preferable to use photo-sensitive film and heat-sensitive film, and examples of the material include silver salt photographic photo-sensitive materials, photo-sensitive heat development materials, various heat-sensitive materials or other such materials which can be used in wet exposure processing and dry exposure processing.

Also, for the image output device of the present invention it is also possible to use such well known image recording devices as an electrophotographic image recording device for transferring an image to image-receiving materials by using photo-sensitive bodies and toner, or an image recording device which uses a format whereby the image is transferred to image-receiving materials by means of a sublimation (ablation) process.

The WS 30 is an output device for using the image data signal of the processed radiation image which has been subjected to the image processing and which was received from the image information processing unit 16 through the network 34, using this image data signal to display the radiation image, which is to be used for the medical diagnosis, displaying this signal on a display screen as a soft copy image in a way such that the signal is either displayed linked to the patient's ID information, or displayed together with a part of this ID information. In the depicted example, the plural numbers of WSs 30 are connected to the image information processing unit 16 through the network 34; however, the present invention is not limited to this configuration, and it is sufficient to have one or more WS 30 units connected. Here, it is also possible to configure the WS 30 so that it receives the image data signal of the unprocessed radiation image which has not yet been subjected to the image processing and which was read by means of the radiation image reading device 24, receiving this signal from the image information processing unit 16 through the network 34, and then displays the signal on the display screen.

The display device of the WS 30 used in the present embodiment is not particularly restricted as long as it can perform display of images for medical diagnosis, and so a CRT display device (i.e., monitor), LCD (monitor) plasma display, electroluminescence panel or other such well known display or monitor may be used. This display device is used for the display of the medical diagnosis, so in order to widen the dynamic range of richness of the display, it is desirable for the brightness to be great, for the display to be capable of high resolution, and for the angle of the breadth of the field of view of the display device to be wide so that more than one doctor or inspection engineer or other such people inspecting the images can view the images simultaneously. In particular, in the case where an LCD is to be used it is desirable to use a display device which is equipped with a mechanism for expanding the breadth of the field of view of the display device.

The image saving device 28 is one type for image output device for storing and saving on a long term basis as an radiation image database at least one of the image data signal of the processed radiation image which has already been subjected to image processing and which was received from the image information processing unit 16 through the network 34 and the image data signal of the unprocessed radiation image before it is subjected to the image processing in relation to the patient's ID information. Here, the image saving device 28 functions as a database of radiation images, so it is desirable to provide this as one type of image output device for the present system; however, if there is no need to provide a database for radiation images, then it is not necessary to provide these. The capacity of the image saving device 28 (i.e., the database capacity) is not particularly restricted, and it is sufficient to select the capacity appropriately in light of the scale of the processing system.

Further, the radiation image data can be stored into the image saving device 28 at any time; however, if the image saving device is also to be given a function of performing backups, then it is good to store the radiation image data at the time when they are temporarily stored to the external storage device 18, but due to circumstances regarding the storage capacity of the image saving device 28, it may be good to save the radiation image data at the time when they are deleted from the external storage device 18. Note that there is no particular limitations on the types of radiation image which are to be stored in the image saving device 28 as the database, and so it is possible to save all the images which are to be saved in the external storage device 18; however, it is also possible to select a portion therefrom to save. The selection of the radiation image which is to be saved into the image saving device 28 can be made at the time when the temporarily saved radiation image is deleted from the external storage device 18.

The IDT 32 is a terminal which is equipped with a keyboard and mouse for inputting, and a monitor, and it is to be used for doing such things as inputting and confirming the patient information, the image capturing information and other such patient ID information, and it can be used, instead of the image information processing unit 16 of the IIP 10A, which is inside the system according to the present embodiment, for doing such things as inputting the patient's ID information, or inputting a portion of the patient's ID information which has not been inputted by means of the image information processing unit 16, then sending this information through the network 34 to the image information processing unit 16 to register it and storing it into the external storage device 18, or using a portion of the patient's ID information which is registered in the image information processing unit 16 to search the external storage device 18 which is connected to the image information processing unit 16, and then cross-checking and confirming a portion of or all of the ID information, or obtaining a portion of or all of the patient's ID information from a magnetic card which has been issued to the patient, and performing searching, cross-checking, confirmation, and the like.

It is also possible to make a reservation for an inspection from the IDT 32. A reservation for an inspection is typically performed by the doctor from one of the WS 30 units in each of the specialist's offices; however, when a prescription for an inspection has been given, for example, there could be cases in which an operator in another department actually performs the input. As described above, in recent years there are many cases in which the inspection generally includes more than one image taken for a given patient, so it is efficient to adopt a method in which the content of the inspection is reserved by means of an input from the IDT 32, and then an engineer from the department specializing in the taking of the images reads out the content of the inspection and makes a reservation for a specific kind of image-taking session. Note that in the actual operations it is good to prepare a screen, such as is described below, which is only used for the purpose of making inspection reservations, and then make selections from this screen in sequence to determine the content of the inspection from selections appearing on the screen, and then input necessary itemized information.

In the case where the invention is to be used frequently in the way described above, it is desirable to arrange the IDT 32 at each of the devices other than the IIP, which means it is arranged at the radiation image capturing device 26, the reception desk in the hospital, the reception desks at each of the specialists' offices, etc., and to thereby facilitate to conduct the input operations and the making of the reservation for the inspection. Additionally, the IDT 32 can be arranged at the radiation image reading device 24, the image output device 22 and the image saving device 28. By adopting this arrangement, the operations of inputting and of reserving the inspection content can become more efficient, and the load on the operator can be alleviated.

Note that a LAN, VAN, or other such format can be used as the construction for the network 34 which connects each of the above-mentioned devices to each other; however, in the present invention there is no particular restriction as to the method by which the network is constructed, and it is possible to use a communications network other than the ones mentioned.

The image information processing system incorporating the image information processing unit thereinto according to the present embodiment is basically constructed as described above, but the operations thereof are explained hereinafter, using as examples the inspection reservation from the IDT 32 and the process of executing the inspection based on this inspection reservation. Note that it is assumed here that a given patient has submitted an inspection prescription to the radiologist's reception desk, and the inspection reservation is to be performed by means of the IDT 32 mentioned above. The operation flow chart depicted in FIG. 3 will be used to explain this in detail.

Figure 3:
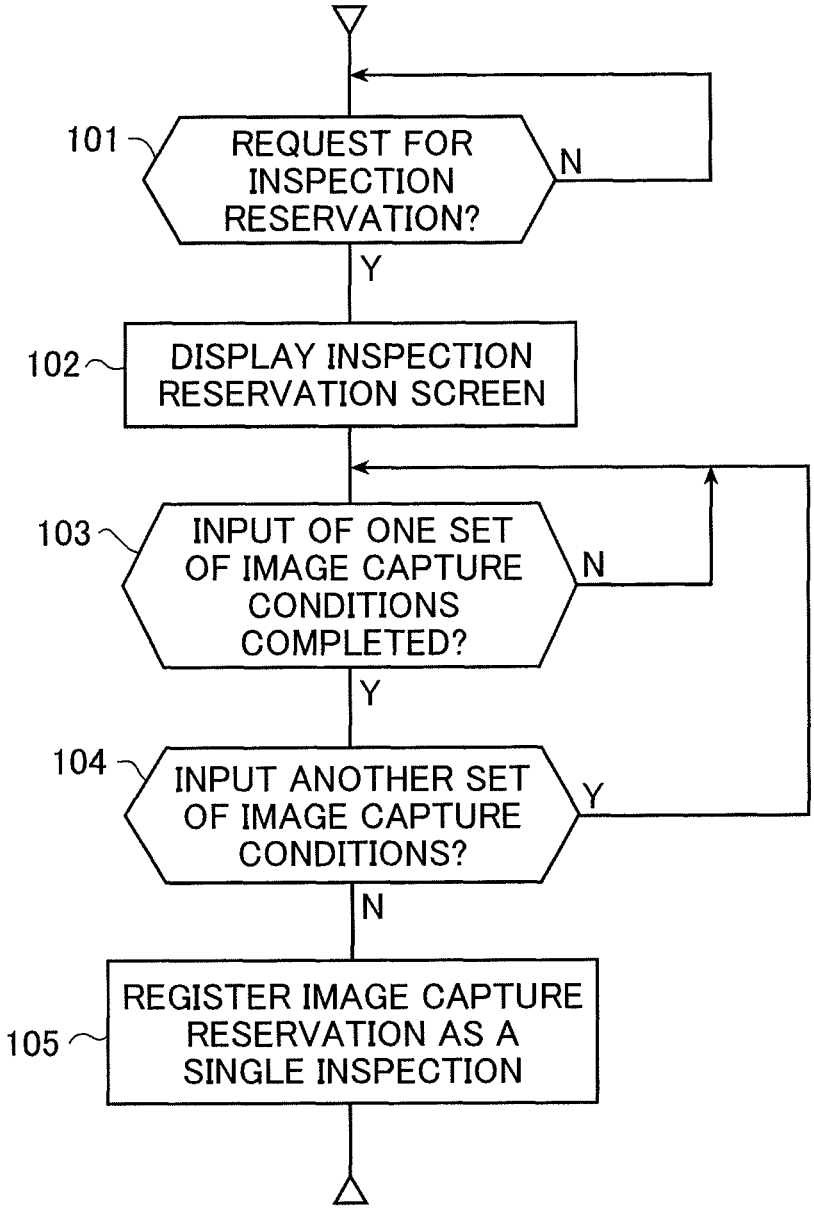
FIG. 3 is an operations flow chart depicting one example of a flow of operations for making a reservation for an inspection from an IDT.

FIG. 3 depicts an operation flow for a reservation for an inspection, which is to be made by using the IDT 32. A function which is inside the image information processing unit 16 and which is for receiving the inspection reservation monitors the inspection reservation request (step 101), and then when there is a request (i.e., case Y at step 101) this function displays an inspection reservation screen (step 102). The operator of the IDT 32 uses this inspection reservation screen to input the image capturing information in sequence, based on inspection content which appears on the inspection reservation screen and which corresponds appropriately to the content to be inspected. At this time, it is sufficient to have the operator typically acknowledge default conditions, and then input conditions by hand only in the case where the operator desires conditions which are different from these default conditions. As described below, the image capturing conditions (of the image capturing information) which are configured here can include a region of the patient which is to be captured, a direction from which the image is to be captured (including so-called AP and PA), a size, and the like.

When one of the image capturing conditions is completely established (i.e., case Y at step 103) then a request is made for the input of the next image capturing condition and this process is repeated (i.e., case Y at steps 103 and 104). When all of the image capturing conditions which have been planned are inputted, then the inspection request receiving function receives and registers these as being for a single inspection (step 105).

The content of the inspection reservation which is inputted as described above is transferred through the network 34 to the IIP 10A. Once the inspection reservation content has been transferred to the IIP 10A, then the content thereof is outputted as a display on the screen of the image display device 20, and also, instructions are automatically given to the radiation image capturing device 26 to capture the image.

FIG. 4 depicts a specific example of the above-mentioned display output screen (referred to as the image capturing screen) 40. According to this example, a reservation is made for the taking of five images, including a frontal thoracic image and others.

That is, in FIG. 4, reference numeral 40a indicates patient information, 40b indicates an image display region, 40c is a tag display indicating the content of what is to be captured (i.e., referred to as a capturing menu), and 40d, 40e and so on each indicate various types of input buttons and instruction buttons. It goes without saying that in the beginning there is no image displayed in the image display region 40b.

At the radiation image capturing device 26, when the image capturing actually starts the images which are captured are sent in sequence to the radiation image reading device 24, and the images are read. Here, as one example, a configuration is adopted in which the image which has been read (i.e., the image before it has been subjected to the image processing by the image information processing unit 16) is displayed in real time, and then when the entire image has been read and the image processing has been completely performed on this image, the above-mentioned image is replaced with the image that has been completely subjected to the image processing; however, the present invention is not limited to this configuration.

Figure 5:
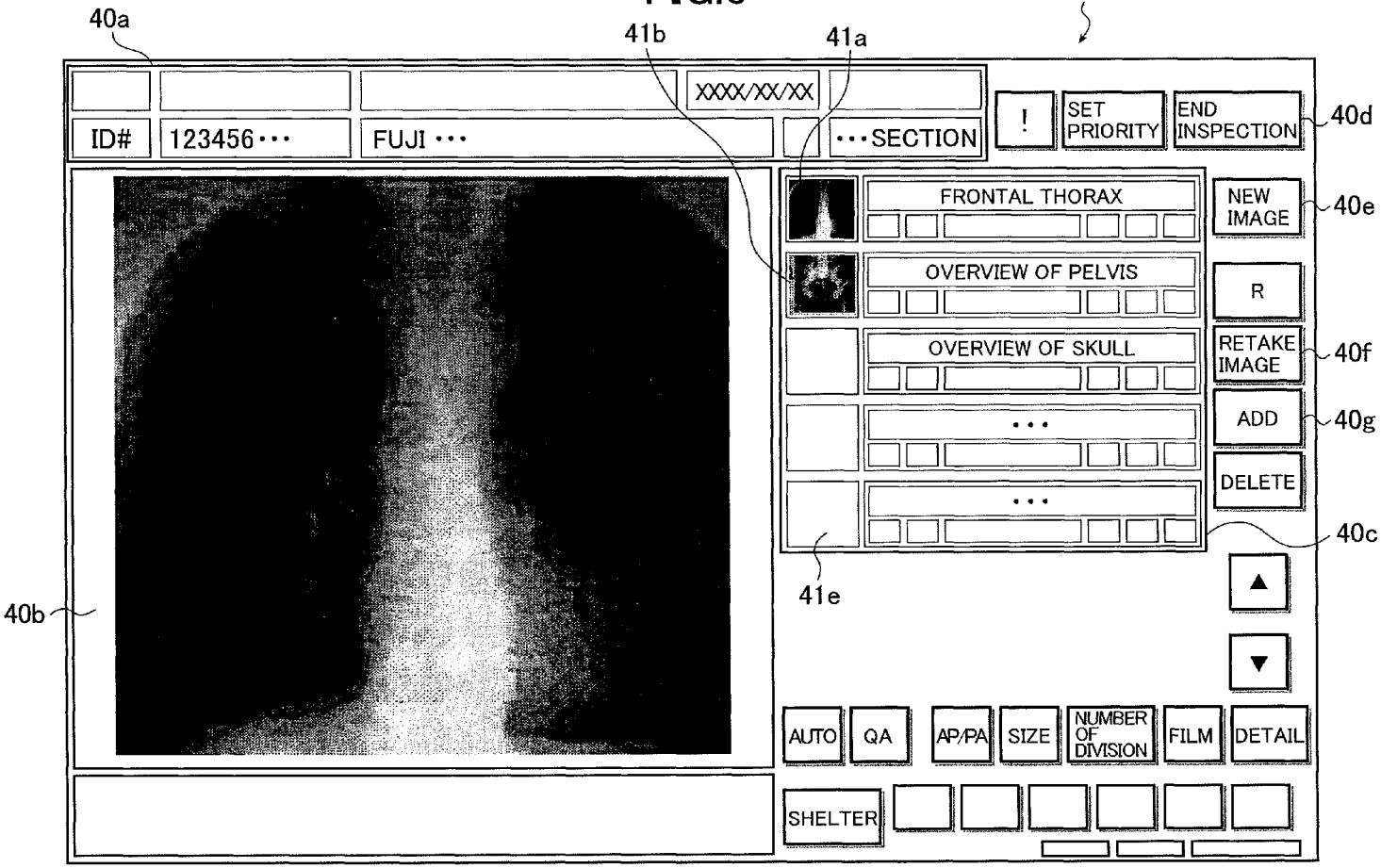
FIG. 5 is a diagram depicting a monitor screen on the image display device inside the IIP as it is in a state when the image capturing has proceeded to a second image.

FIG. 5 depicts a monitor screen as it is in the state when the image capturing has proceeded to the second image. What is depicted in FIG. 5 is the situation in which a single frontal thoracic image which has been subjected to the image processing and was captured as a first image is displayed in the image display region 40b, and at the present time, the second image capture has been completed and the image processing is being performed on this second image by the image information processing unit 16. Note that in the present embodiment, once the entire image has been read out then thumbnail images (i.e., reduced-size versions) 41a to 41e are created, and these thumbnail images are displayed in the front portion of the capture menu to which that thumbnail image corresponds among the above plurality of capture menus. In FIG. 5, the thumbnail image of the image which corresponds to the second image capture is being displayed.

A comparison of the capture menu columns in FIG. 4 and FIG. 5 reveals that the capture menu in FIG. 4 indicates that the second image was taken of an external view of the skull area; however, in FIG. 5 the second image was taken of an external view of the pelvis area. This is a necessary point to notice. According to the procedure for capturing the radiation images, the image which is easiest to take after the first image of the frontal thorax is given precedence, and so, as a result, in this case the capture menu (i.e., tags) are reordered on the image display screen 20 so that they correspond with the order in which the images are captured. This is effective for making it easy to determine how much of the entire image capturing work has been completed; however, the present invention is not necessarily limited to this configuration.

Note that the above-mentioned reordering of the capture menu (i.e., the tags) can also be performed in the case where the image is captured in a mistaken order. In such a case, in order to modify the relationship or the correspondences between the thumbnail images and the capture menu (i.e., tags), it is possible to apply a method in which the two thumbnail images which ought to be reordered are reordered by giving instructions for them, another method in which the thumbnail images which ought to be reordered are dragged (i.e., pulled and made to move) to the positions they would be in after the reordering, or the like.

Further, in FIG. 5, an image for which the results of the second image capture are not yet being indicated is not yet being displayed because it is being subjected to the image processing at the image information processing unit 16, and only the thumbnail image thereof is being displayed. This is to provide detailed information about the progress of the capturing of the images, and it is also effective for discovering mistakes in the image capturing (i.e., such as taking images of the wrong region, taking images from the wrong angle) at an early stage.

When other instruction buttons depicted in FIG. 5 are pressed, for example, an "end inspection" button 40d, a "new image" button 40e, a "retake image" button 40f, an "add" button 40g, then an application which corresponds to each of these buttons is booted, and the desired process is executed. Hereinafter, several examples thereof will be given.

Figure 6:
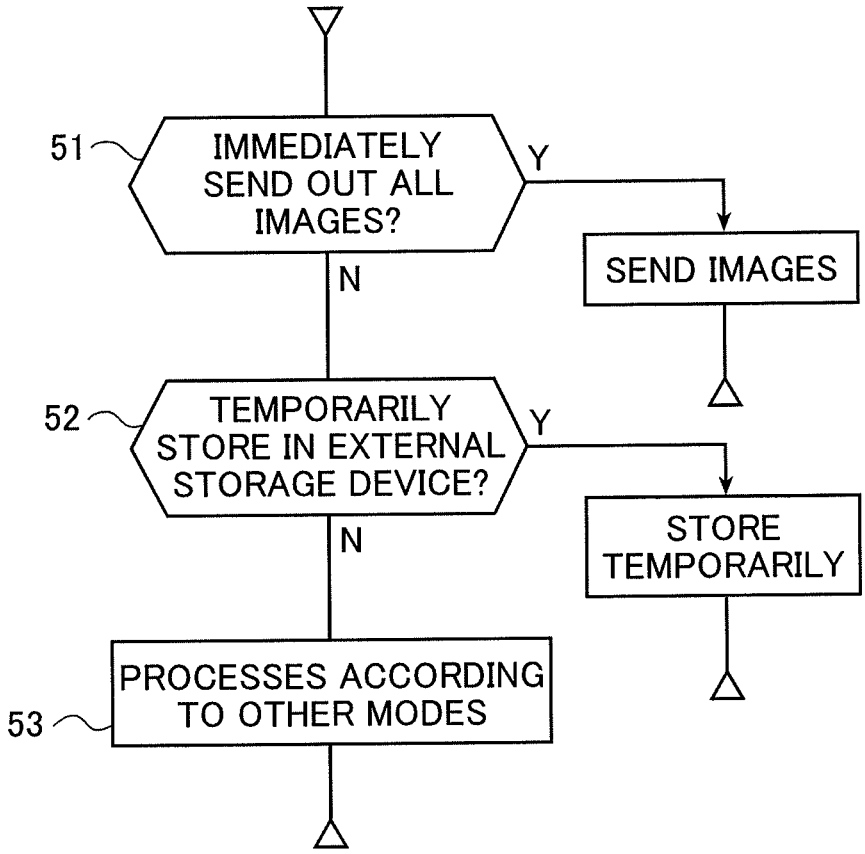
FIG. 6 is a diagram depicting one example of operations in a case where an "end inspection" button depicted in FIG. 5 is pressed.

In the case where the "end inspection" button 40d is pressed, an operation such as the one depicted in FIG. 6 or the like is performed. Namely, the image is outputted together with an image output mode which is to be performed at the end of the inspection. Examples of this image output mode include a sending mode in which all of the images are sent through the network 34 to a designated WS 30 (which is at the specialist's office which requested the image to be taken) (step 51), a mode in which the image is temporarily stored in the external storage device 18 (step 52) or other modes (step 53).

Figure 7:
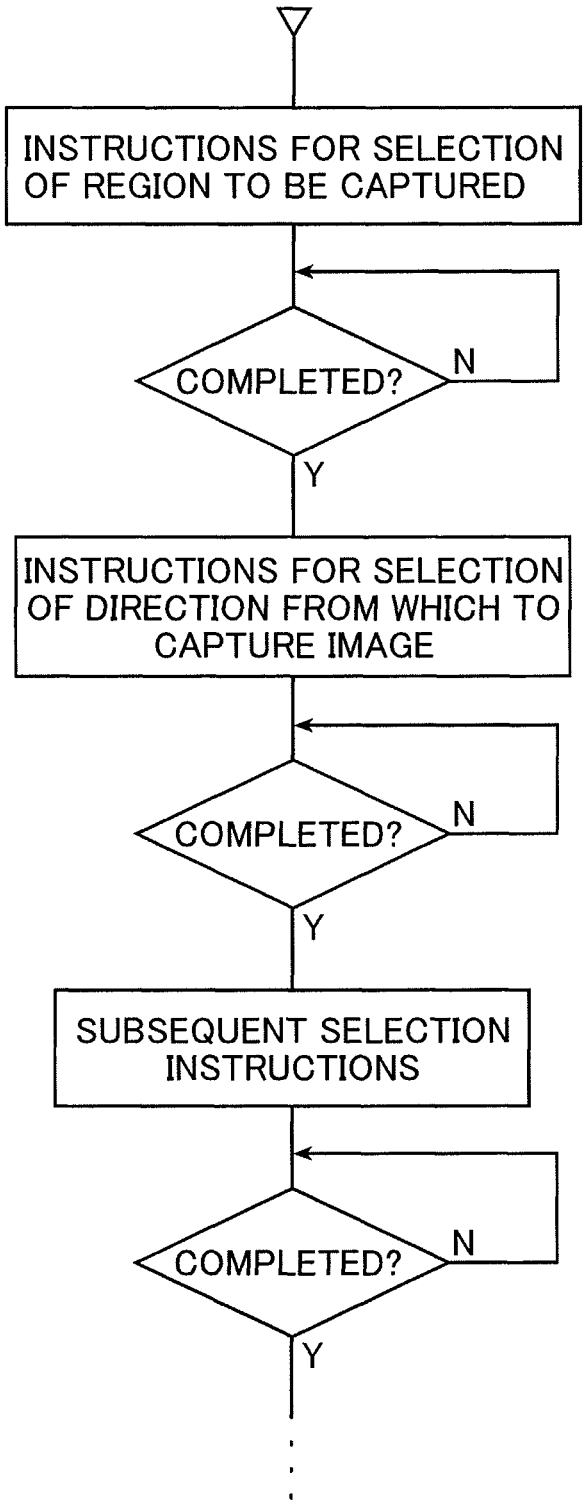
FIG. 7 is a diagram depicting one example of operations in a case where an "new image" button depicted in FIG. 5 is pressed.

The "new image" button 40e is for inputting instructions in the case where, for example, a new image capture is to be added which does not use the same image capture conditions which had been used up until that point. When this button is pressed, screens are displayed one after another for selecting conditions ranging from such things as the new region to be captured, to the angle and size of the image to be captured, so the operator only has to respond to these screens to set the new capture conditions. FIG. 7 depicts one example of the process flow.

Figure 8:
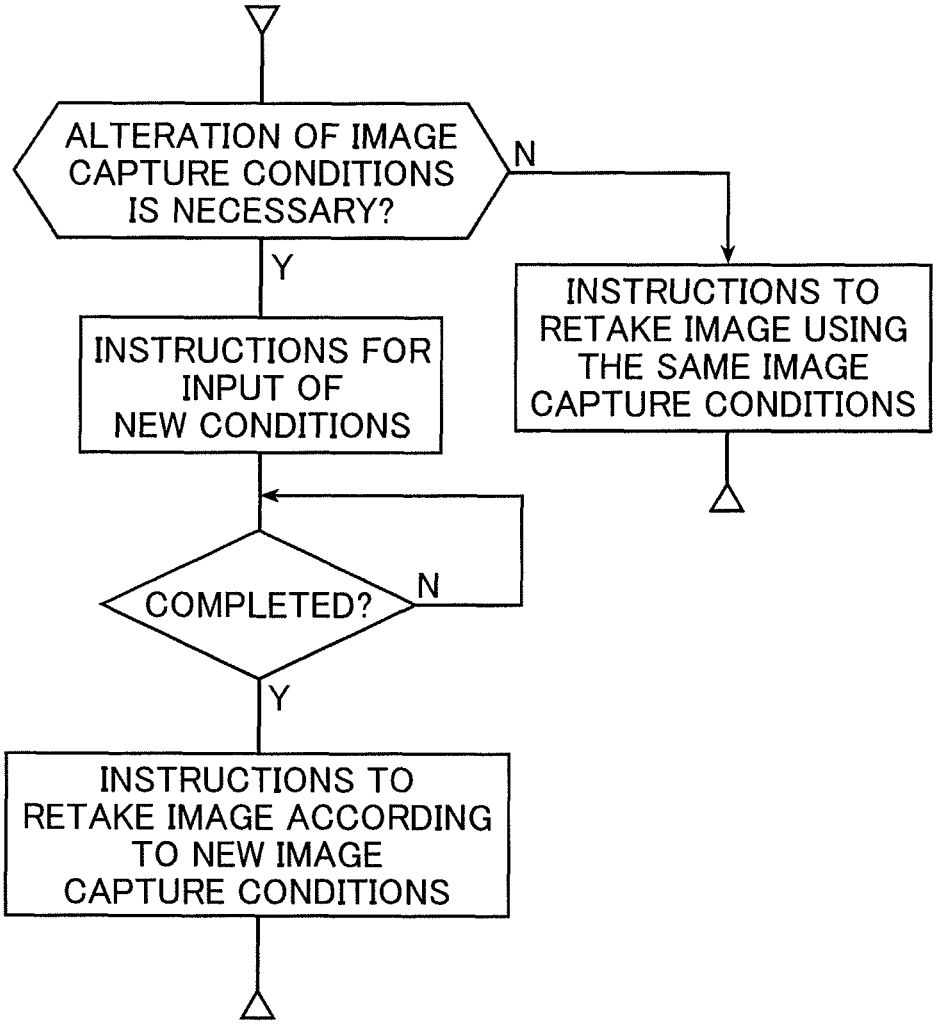
FIG. 8 is a diagram depicting one example of operations in a case where an "retake image" button depicted in FIG. 5 is pressed.

The "retake image" button 40f is used when the operator sees the image which has been captured and displayed, notices that there is some sort of mistake, and wants to change the image capture conditions (i.e., such as in the case where the original settings were not correct, or because the operator discovered better image capture conditions after taking the image), or wants to retake the image without changing the image capture conditions (i.e., such as in the case where the subject moved inadvertently during the taking of the image). FIG. 8 depicts one example of this process flow.

The "add" button 40g is used in the case where an image capture is to be added in a similar fashion as in the case of the "new image" button 40e, but the difference from the case of the "new image" button 40e is that this button is an effective button in the case where the operator wishes to increase the quantity of the images captured using the same image capture conditions (i.e., such as the case where contrast media or such are used in the taking of the image, but the speed at which the contrast media are to move is predicted inaccurately as images are captured one after the other while the contrast media are moved).

Similar instruction buttons can be increased one after another as needed, and the content of the programs associated with the buttons can be altered appropriately.

Further, numbers can be applied to the image capture menu in sequence along the image capture menu (i.e., tags) array such as those depicted in the above-mentioned display screen (see FIG. 5, etc.), and this can be used effectively to produce the result that one image from among images from a single inspection can be designated in connection with these numbers, in order to use these numbers to specify an order in which the display output is to be performed or in which the hard copies are to be made.

Note that the above embodiment is one example of the present invention, and, of course, the present invention is not limited to this embodiment, but various improvements and alterations can be made without departing from the essential scope of the present invention.

For example, in the above embodiment an example of the present invention is given in which the image information processing system includes the IIP which is connected to the network; however, the present invention can be used with an independent structure, as well.

As described in detail above, the present invention provides an image and information processor which can be used preferably even in the case where a single inspection uses several or more images, and it achieves an obvious effect such that when the images are to be handled they can be handled in units going from one image at a time to several or more images which are to be used in connection with a single inspection.

More specifically, whether the image and information processor is in the independent structure (stand-alone) or is connected to the network, the sequence of operations during the course of the inspection can be executed easily in either case, including the configuration of the image capture conditions (image capturing information) which are to be the content of the inspection, the step-by-step monitoring of the progress of the image capturing, the giving of the instructions for the image to be retaken in the case where a mistake is discovered, and thus a significant improvement becomes possible with respect to the efficiency with which the radiation images for the inspection are handled.

What is claimed is:

1. An image and information processor comprising:

an image information processing unit having a function for inputting patient information and radiation image capture information related to said patient information; a function for receiving at least one first radiation image having been read by means of a radiation image reading device; and a function for performing image processing on said at least one first radiation image having been received from said radiation image reading device;

an image display device which is connected to said image information processing unit and displays at least one of said at least one first radiation image and at least one second radiation image having been subjected to said image processing by said image information processing unit; and an external storage device which is connected to said image information processing unit and stores temporarily at least one of said at least one first radiation image and said at least one second radiation image in relation to said patient information; wherein said image information processing unit is constructed such that a serial radiography based on a plurality of radiographic conditions of said image capture information relating to one patient inputted by means of said input function can be reserved as a single inspection,

*said plurality of radiographic conditions of said radiation image capture information which are reserved as said single inspection are displayed in a single screen of said image display device as tags, each corresponding to each of said plurality of radiographic conditions,*

*each of predetermined regions corresponding in a one-to-one manner to each of said tags and displaying a thumbnail image of a radiation image corresponding to each of said plurality of radiographic conditions, is displayed in advance in a region adjacent to a region in which each of said plurality of radiographic conditions is displayed, and,*

*when said serial radiography is begun and the radiation image corresponding to each of said plurality of radiographic conditions is stored, said thumbnail image of said radiation image is displayed in a predetermined region of said predetermined regions corresponding to a tag of said tags.*

2. The image and information processor according to claim 1, wherein said image information processing unit is connected via a network to said radiation image reading device or radiation image reading devices and one or more image output devices for outputting said at least one second radiation image.

[3. The image and information processor according to claim 1, wherein said plurality of radiographic conditions of said radiation image capture information which are reserved as said single inspection are displayed in a single screen as tags, each corresponding to each of said plurality of radiographic conditions.]

[4. The image and information processor according to claim 3, wherein when said serial radiography is begun and the radiation image corresponding to each of said plurality of radiographic conditions is stored, a thumbnail image of said radiation image is displayed in relation to a tag of said tags.]

5. The image and information processor according to claim [4] *1*, wherein a relationship between said tag and said thumbnail image can be altered or exchanged by moving said thumbnail image that has been displayed related to said tag.

6. [An] *The* image and information processor according to claim [3] *1*, wherein consecutive numbers are assigned to radiation images pertaining to said single inspection according to order that said tags are arranged in, and this display sequence in which said radiation images are displayed is controlled by said consecutive numbers.

7. The image and information processor according to claim [3] *1*, wherein consecutive numbers are assigned to radiation images pertaining to said single inspection according to order that said tags are arranged in, and when said radiation images are outputted, this output sequence is controlled by said consecutive numbers.

8. The image and information processor of claim 1, *further comprising an ID input terminal providing an inspection prescription* wherein the single inspection is reserved based on [an] *the* inspection prescription.

9. The image and information processor of claim 1, wherein the [image capturing conditions] *plurality of radiographic conditions of said image capture information* include at least one of a region of a patient to be captured, a direction from which the at least one first radiation image is to be captured, an orientation for image capture, and size.

10. The image and information processor of claim 9, wherein an order of [image capture conditions] *the plurality of radiographic conditions of said image capture information* progresses in order of difficulty of image capture.

11. An image and information processor, comprising:

one or more radiation image reading devices for reading a radiation image;

an image information processing unit having a function for inputting patient information and radiation image capture information related to said patient information; a function for receiving at least one first radiation image having been read by means of one or more radiation image reading devices; and a function for performing image processing on said at least one first radiation image having been received from said one or more radiation image reading devices;

an image display device which is connected to said image information processing unit and displays at least one of said at least one first radiation image, and at least one second radiation image having been subjected to said image processing by said image information processing unit; and an external storage device which is connected to said image information processing unit and stores temporarily at least one of said at least one first radiation image and said at least one second radiation image in relation to said patient information; wherein said image information processing unit is connected via a network to said one or more radiation image reading devices and one or more image output devices for outputting said at least one second radiation image; and wherein said image information processing unit is constructed such that a serial radiography based on a plurality of radiographic conditions of said radiation image capture information relating to one patient inputted by means of said input function can be reserved as a single inspection,

*said plurality of radiographic conditions of said radiation image capture information which are reserved as said single inspection are displayed in a single screen as tags, each corresponding to each of said plurality of radiographic conditions,*

*each of predetermined regions corresponding in a one-to-one manner to each of said tags and displaying a thumbnail image of a radiation image corresponding to each of said plurality of radiographic conditions, is displayed in advance in a region adjacent to a region in which each of said plurality of radiographic conditions is displayed, and*

*wherein when said serial radiography is begun and the radiation image corresponding to each of said plurality of radiographic conditions is stored, said thumbnail image of said radiation image is displayed in a predetermined region of said predetermined regions corresponding to a tag of said tags.*

*12. The image and information processor according to claim 1, wherein a frame for specifying a region for displaying said thumbnail image is provided in each of said predetermined regions.*

*13. The image and information processor according to claim 1, wherein nothing is displayed in each of said predetermined regions until when the radiation image corresponding to each of said plurality of radiographic conditions is stored.*

*14. The image and information processor according to claim 1, wherein said predetermined regions are blank regions.*

*15. The image and information processor according to claim 11, wherein a frame for specifying a region for displaying said thumbnail image is provided in each of said predetermined regions.*

*16. The image and information processor according to claim 11, wherein nothing is displayed in each of said predetermined regions until when the radiation image corresponding to each of said plurality of radiographic conditions is stored.*

*17. The image and information processor according to claim 11, wherein said predetermined regions are blank regions.*

* * * * *